(12) United States Patent
Inada et al.

(10) Patent No.: US 11,577,098 B2
(45) Date of Patent: Feb. 14, 2023

(54) CONTROL APPARATUS

(71) Applicant: SONIRE THERAPEUTICS INC., Tokyo (JP)

(72) Inventors: Seisho Inada, Kariya (JP); Tsuyoshi Ueyama, Kariya (JP); Hideki Okuda, Kariya (JP); Toshihiko Koyama, Kariya (JP)

(73) Assignee: SONIRE THERAPEUTICS INC., Tokyo (JP)

( * ) Notice: Subject to any disclaimer, the term of this patent is extended or adjusted under 35 U.S.C. 154(b) by 2 days.

(21) Appl. No.: 16/872,847

(22) Filed: May 12, 2020

(65) Prior Publication Data

US 2020/0269074 A1    Aug. 27, 2020

Related U.S. Application Data

(63) Continuation of application No. PCT/JP2018/043040, filed on Nov. 21, 2018.

(30) Foreign Application Priority Data

Nov. 27, 2017    (JP) .............................. JP2017-226981

(51) Int. Cl.
*A61B 8/00* (2006.01)
*A61N 7/02* (2006.01)
(Continued)

(52) U.S. Cl.
CPC .............. *A61N 7/02* (2013.01); *A61B 8/4245* (2013.01); *A61B 8/54* (2013.01); *A61B 34/37* (2016.02);
(Continued)

(58) Field of Classification Search
CPC .............. A61N 7/02; A61N 2007/0034; A61N 2007/0065; A61B 90/03; A61B 8/4245; A61B 8/54; A61B 2090/033; A61B 2562/0247; A61B 90/50; A61B 2090/064; A61B 8/463; A61B 8/5292; A61B 8/461; A61B 8/469; A61B 8/465; A61B 8/085; A61B 8/5223; A61B 8/5269; A61B 8/5276; A61B 8/4218; A61B 34/37
See application file for complete search history.

(56) References Cited

U.S. PATENT DOCUMENTS

2005/0154431 A1 *  7/2005  Quistgaard ............ A61B 34/32
                                                           607/96
2013/0158411 A1    6/2013  Miyasaka
(Continued)

FOREIGN PATENT DOCUMENTS

FR          3072577 B1 *  9/2019  .............. A61N 7/02
JP          H05-76538 A   3/1993
(Continued)

*Primary Examiner* — Christopher Koharski
*Assistant Examiner* — Taylor Deutsch
(74) *Attorney, Agent, or Firm* — Harness, Dickey & Pierce, P.L.C.

(57) ABSTRACT

A control apparatus detects a misalignment between an irradiation position of a transdermal treatment device and a target irradiation position. When the misalignment is detected, the control unit stops irradiation of the transdermal treatment device or moves the irradiation position closer to the target irradiation position.

2 Claims, 10 Drawing Sheets

(51) Int. Cl.
*A61B 34/37* (2016.01)
*A61B 90/00* (2016.01)
*A61N 7/00* (2006.01)
*A61B 90/50* (2016.01)

(52) U.S. Cl.
CPC ............ *A61B 90/03* (2016.02); *A61B 8/4218* (2013.01); *A61B 90/50* (2016.02); *A61B 2090/033* (2016.02); *A61B 2090/064* (2016.02); *A61B 2562/0247* (2013.01); *A61N 2007/0034* (2013.01)

(56) References Cited

U.S. PATENT DOCUMENTS

| | | |
|---|---|---|
| 2018/0185103 A1 | 7/2018 | Mukumoto et al. |
| 2019/0054324 A1 | 2/2019 | Tsutsumi |

FOREIGN PATENT DOCUMENTS

| | | |
|---|---|---|
| JP | H09-066057 A | 3/1997 |
| JP | H09-248213 A | 9/1997 |
| JP | 2000-237205 A | 9/2000 |
| JP | 2000271136 A | 10/2000 |
| JP | 2007196037 A | 8/2007 |
| JP | 2010207427 A | 9/2010 |
| JP | 2014094172 A | 5/2014 |
| JP | 2017023339 A | 2/2017 |
| JP | 2019093002 A | 6/2019 |
| WO | WO-2014155556 A1 | 10/2014 |
| WO | WO-2017/138090 A1 | 8/2017 |

\* cited by examiner

CONTROL APPARATUS

CROSS REFERENCE TO RELATED APPLICATIONS

The present application is a continuation application of International Patent Application No. PCT/JP2018/043040 filed on Nov. 21, 2018, which designated the U.S. and claims the benefit of priority from Japanese Patent Application No. 2017-226981 filed on Nov. 27, 2017. The entire disclosures of all of the above applications are incorporated herein by reference.

TECHNICAL FIELD

The present disclosure relates to a control apparatus.

BACKGROUND

A HIFU (High Intensity Focused Ultrasound) treatment system includes an irradiation unit that irradiates the ultrasound. The ultrasound emitted from the irradiation unit focus on a focal point. Before irradiating the ultrasound, the operator moves the irradiation unit such that the irradiation position of the ultrasound coincides with a target irradiation position. The target irradiation position is an affected portion to be treated. Methods of confirming the irradiation position include a method using an ultrasound diagnostic probe, a method using MRI, and the like.

SUMMARY

According to an aspect of the present disclosure, a control apparatus detects a misalignment between an irradiation position of a transdermal treatment device and a target irradiation position. In response to detecting a misalignment, the control unit stops the irradiation of the transdermal treatment device or to brings the irradiation position closer to the target irradiation position.

DETAILED DESCRIPTION

Hereinafter, embodiments of the present disclosure will be described with reference to the drawings.

1. Configuration of Treatment System 1

Figure 1:
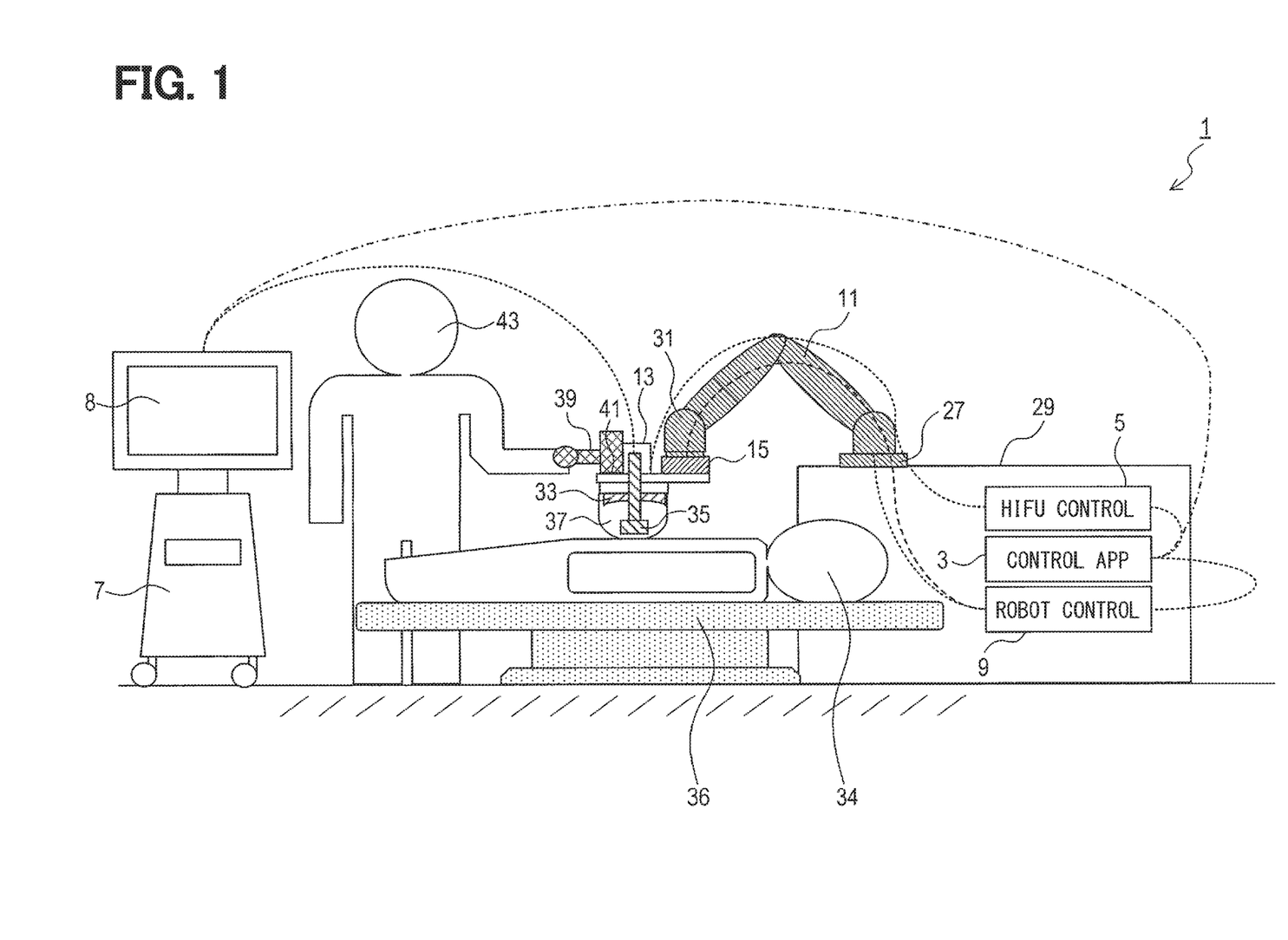
FIG. 1 is an explanatory diagram illustrating a configuration of a treatment system.
Figure 2:
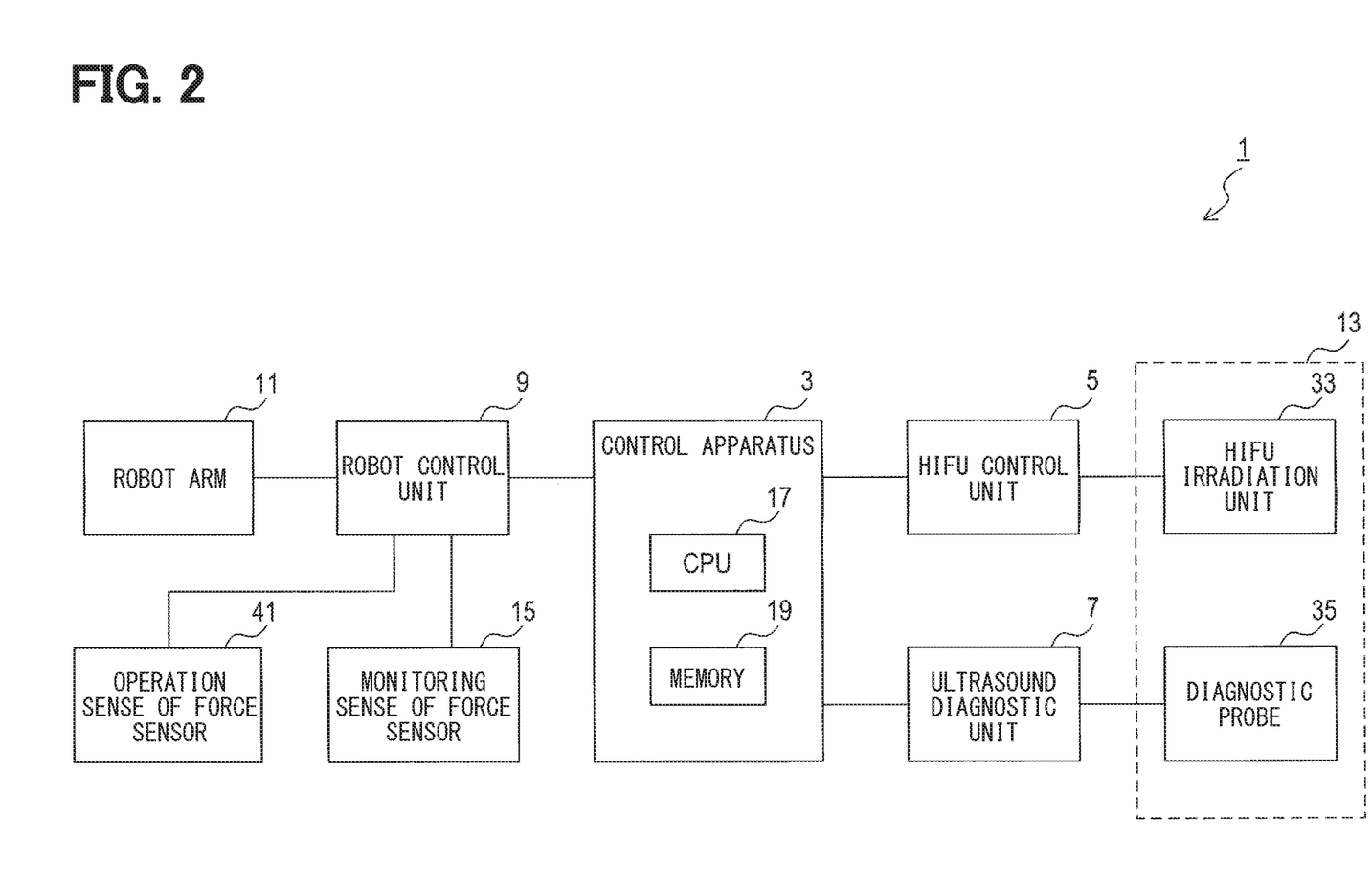
FIG. 2 is a block diagram illustrating an electrical configuration of a treatment system.

The configuration of a treatment system 1 will be described with reference to FIGS. 1 to 3. As shown in FIGS. 1 and 2, the treatment system 1 includes a control apparatus 3, a HIFU control unit 5, an ultrasound diagnostic unit 7, a robot control unit 9, a robot arm 11, a tip unit 13, and a monitoring sense of force sensor 15. The monitoring sense of force sensor 15 corresponds to a force detection device.

Figure 3:
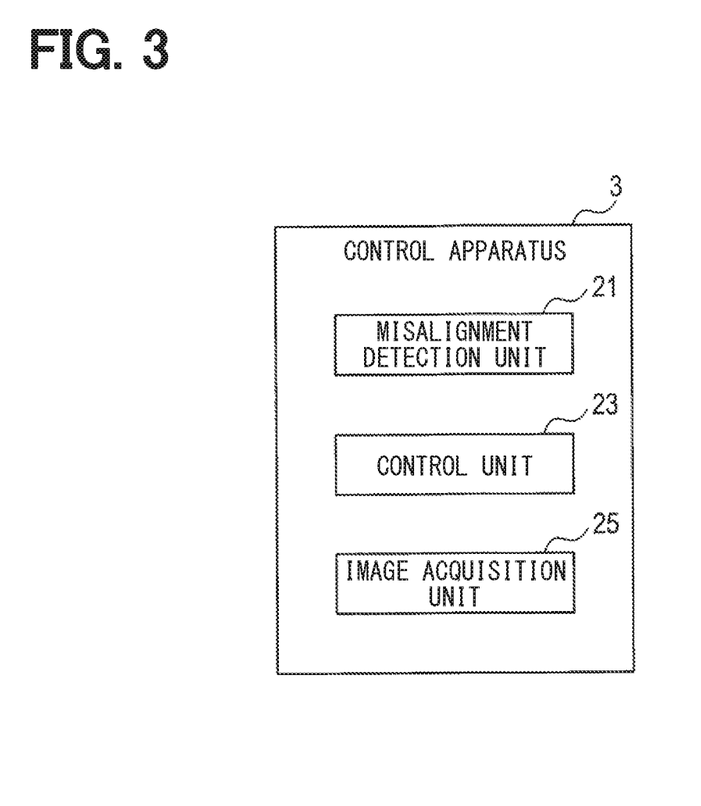
FIG. 3 is a block diagram illustrating a functional configuration of a control apparatus.

The control apparatus 3 includes a misalignment detection unit 21, a control unit 23, and an image acquisition unit 25, as shown in FIG. 3. The control apparatus 3, which may also be referred to as a controller or a control circuit, includes a microcomputer (i.e., computer). The control apparatus 3 may be provided as one microcomputer (i.e., computer), or a plurality of microcomputers (i.e., computers).

The technique for realizing the functions of each unit included in one or more computers in the control apparatus 3 is not limited to software, and some or all of the functions may be realized using one or more hardware circuits. For example, when the above-described functions may be implemented by an electronic circuit which is hardware, the electronic circuit may be implemented by a digital circuit, an analog circuit, or a combination thereof. In other words, the computer or controller serving as the control apparatus 3 may be configured by (i) a central processing unit (CPU) along with memory storing instructions (i.e., computer program) executed by the CPU, or (ii) hardware circuitry including a digital circuit and/or an analog circuit such as an integrated circuit or hard-wired logic circuit with no CPU, or (iii) both the CPU along with memory and the hardware circuitry.

As an example of the present embodiment, as shown in FIG. 2, the control apparatus 3 includes a microcomputer having a CPU 17 and a semiconductor memory such as a RAM or a ROM (hereinafter, referred to as a memory 19). In this example, respective functions of the microcomputer in the control apparatus 3 are realized by the CPU 17 executing a program stored in a non-transitory tangible storage medium. In this example, the memory 19 corresponds to a non-transitory tangible storage medium in which the programs are stored. A method corresponding to the program is executed by the execution of the program.

The HIFU control unit 5 includes an amplifier of a HIFU irradiation unit 33 described later. The HIFU control unit 5 starts and stops the irradiation of the ultrasound by the HIFU irradiation unit 33. Further, the HIFU control unit 5 adjusts the output of the ultrasound radiated by the HIFU irradiation unit 33.

The ultrasound diagnostic unit 7 acquires an ultrasound image using a diagnostic probe 35 described later. The ultrasound image is an image representing an inside of the body of the patient 34. The ultrasound diagnostic unit 7 has a monitor 8. The ultrasound diagnostic unit 7 can display an ultrasound image on the monitor 8.

The robot control unit 9 controls the operation of the robot arm 11. As shown in FIG. 1, the base 27 of the robot arm 11 is fixed to a table 29. The tip unit 13 and the monitoring sense of force sensor 15 are attached to the tip portion 31 of the robot arm 11. The robot arm 11 can change the position of the tip unit 13 and the monitoring sense of force sensor 15 by movement. The robot arm 11 can press a water bag 37, which will be described later, of the tip unit 13 against the body of the patient 34. The patient 34 is lying on a bed 36. The monitoring sense of force sensor 15 detects a force applied by the body of the patient 34 to the tip unit 13.

The tip unit 13 includes a HIFU irradiation unit 33, a diagnostic probe 35, a water bag 37, an operation unit 39, and an operation sense of force sensor 41. The HIFU irradiator 33 irradiates the body of the patient 34 with the ultrasound (hereinafter referred to as focused ultrasound) focused on the focal point. The HIFU irradiation unit 33 and the HIFU control unit 5 correspond to a transdermal treatment device and a focused ultrasound irradiation device. A transdermal treatment device is a device that radiates ultrasound, radiant ray, and the like to the inside of the body of the patient from the outside. The focused ultrasound irradiation device is a device that irradiates ultrasound focused on a focal point inside of the body of the patient from outside. The water bag 37 is located between the HIFU irradiation unit 33 and the patient 34. The water bag 37 is pressed against the patient 34.

The diagnostic probe 35 creates an ultrasound image representing the inside of the body of the patient 34 using ultrasound. The visual field of the ultrasound image has a fixed positional relationship with the position (hereinafter referred to as irradiation position F) where the HIFU irradiation unit 33 irradiates the focused ultrasound. The diagnostic probe 35 sends an ultrasound image to the ultrasound diagnostic unit 7.

The operation unit 39 is a handle that can be gripped by the operator 43. The operation unit 39 is operated by the operator 43. The operation sense of force sensor 41 detects the magnitude and direction of the force applied to the operation unit 39 by the operator 43. The robot control unit 9 operates the robot arm 11 according to the magnitude and direction of the force detected by the operation sense of force sensor 41.

2. Processing Executed by Control Apparatus 3

The processing executed by the control apparatus 3 will be described with reference to FIGS. 4 to 7. This processing is executed after the operator 43 determines a position to be irradiated with the focused ultrasound (hereinafter, referred to as a target irradiation position T) and starts irradiation of the focused ultrasound toward the target irradiation position T. The operator 43 can search for the target irradiation position T while viewing the ultrasound image displayed on the monitor 8. The target irradiation position T is at a fixed position with respect to the body of the patient 34.

Figure 4:
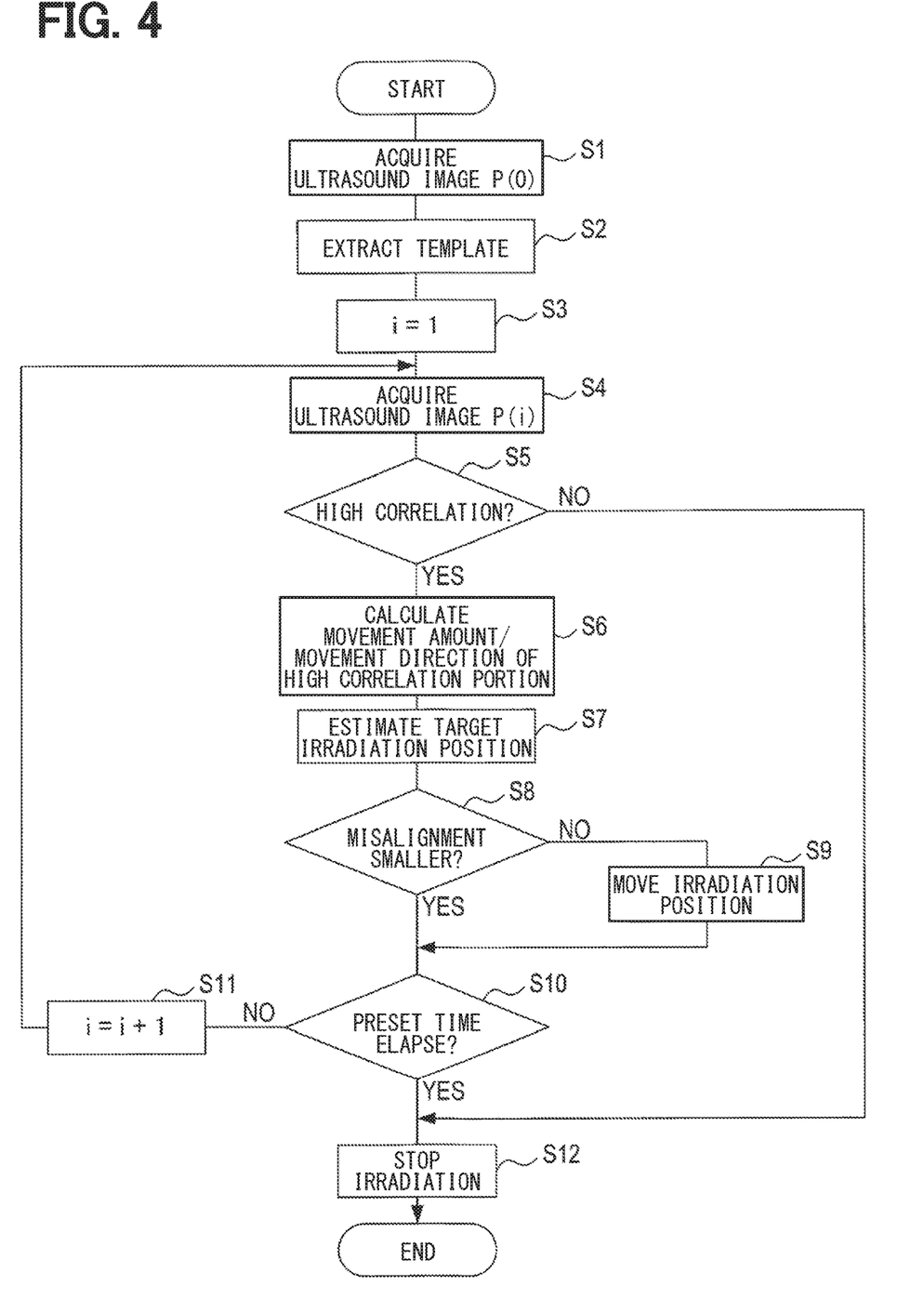
FIG. 4 is a flowchart illustrating a process executed by a control apparatus.
Figure 5:
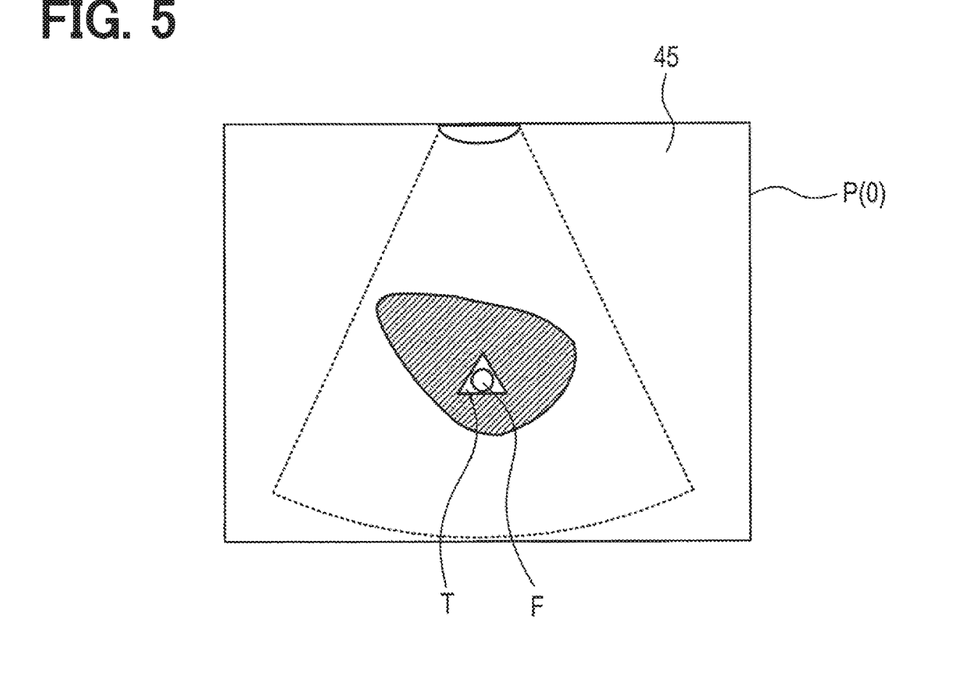
FIG. 5 is an explanatory diagram illustrating an ultrasound image.

In step 1 of FIG. 4, the image acquisition unit 25 acquires an ultrasound image using the ultrasound diagnostic unit 7 and the diagnostic probe 35. The ultrasound image acquired here is P(0). FIG. 5 shows an example of the ultrasound image P(0). The ultrasound image P(0) represents a portion of the body of the patient 34. The irradiation position F is in the visual field 45 of the ultrasound image P(0). The positional relationship of the irradiation position F with respect to the visual field 45 is fixed. In the ultrasound image P(0), the position of the HIFU irradiation unit 33 is adjusted such that the target irradiation position T and the irradiation position F match.

Figure 6:
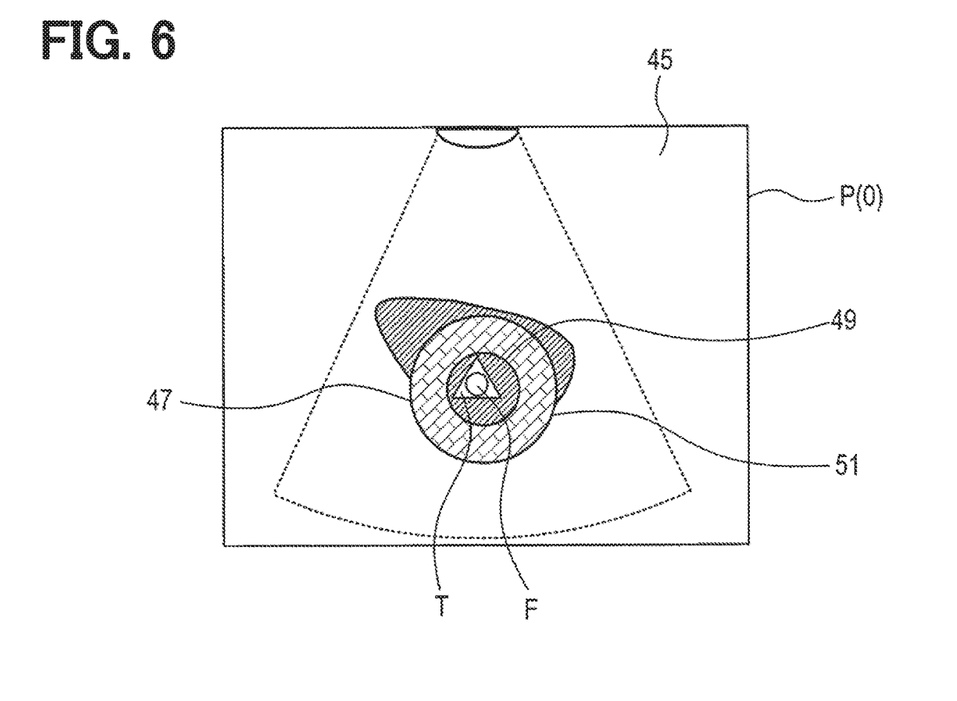
FIG. 6 is an explanatory diagram illustrating an ultrasound image and a template.

In Step 2, the misalignment detection unit 21 extracts the template 47 from the ultrasound image P(0) as shown in FIG. 6. The template 47 is a partial area of the ultrasound image P(0). The misalignment detection unit 21 extracts the template 47 from a portion excluding the irradiation position F in the ultrasound image P(0). The shape of the template 47 is, for example, a region between the inner circle 49 and the outer circle 51. The template 47 is at a fixed position with respect to the body of the patient 34.

In step 3, the image acquisition unit 25 sets i to 1. Here, i is a number assigned to the ultrasound image.

In Step 4, the image acquisition unit 25 acquires the ultrasound image P(i) using the ultrasound diagnostic unit 7 and the diagnostic probe 35. The ultrasound image P(i) is the i-th ultrasound image acquired in Step 4. The shape and size of the visual field 53 of the ultrasound image P(i) are the same as the shape and size of the visual field 45.

The positional relationship of the irradiation position F with respect to the visual field 45 and the positional relationship of the irradiation position F with respect to the visual field 53 are the same. Therefore, when the ultrasound image P(0) and the ultrasound image P(i) are overlapped, the irradiation position F in the ultrasound image P(0) is the same as the irradiation position F in the ultrasound image P(i).

Figure 7:
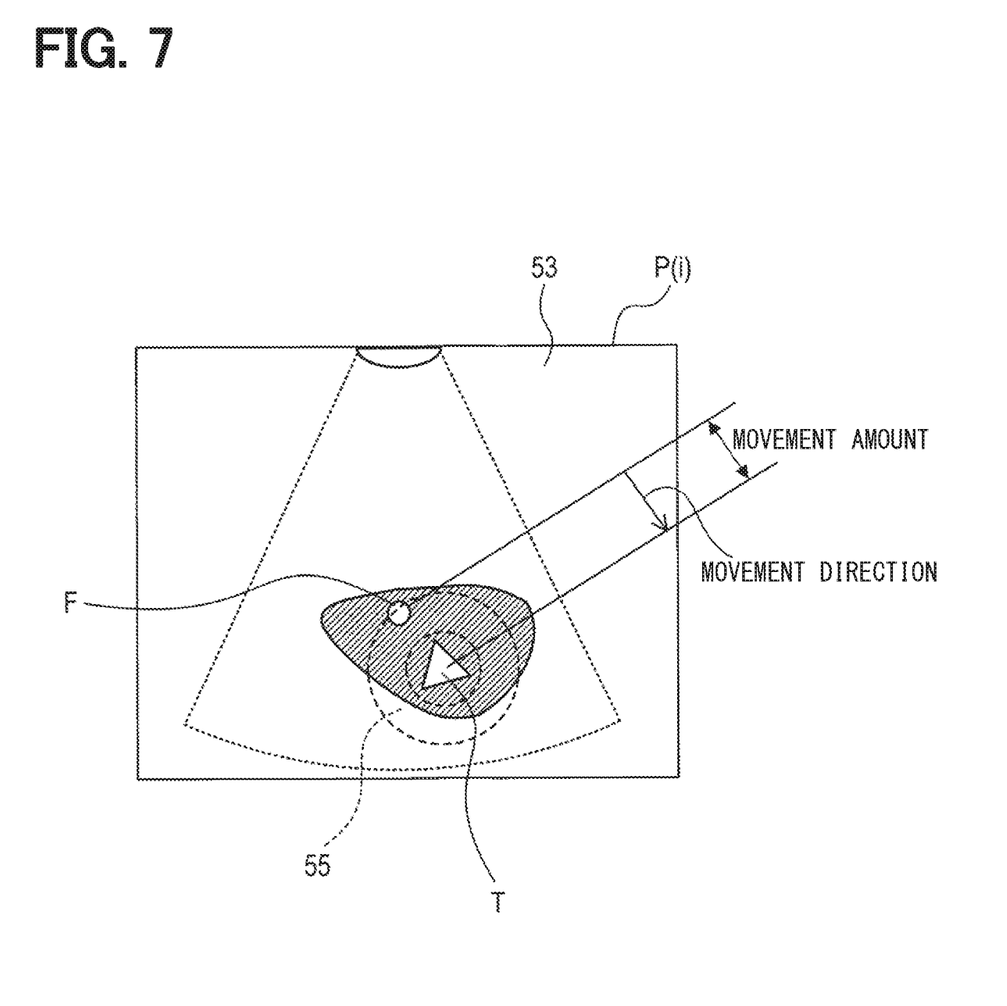
FIG. 7 is an explanatory diagram illustrating an ultrasound image.

In step 5, the misalignment detection unit 21 searches the ultrasound image P(i) for a portion (hereinafter referred to as a high correlation portion 55) having a high correlation with the template 47 extracted in step 2. FIG. 7 shows an example of the high correlation portion 55. The high correlation portion 55 is, for example, a portion where the correlation coefficient with the template 47 is larger than a preset threshold. The high correlation portion 55 is a portion of the body of the patient 34 that is likely to be the same as the portion represented by the template 47. That is, the high correlation portion 55 corresponds to a portion corresponding to the template 47 in the ultrasound image P(i).

If the misalignment detection unit 21 can find the high correlation portion 55 in the ultrasound image P(i), the process proceeds to step 6 and the misalignment detection unit 21 sets the high correlation portion 55 in the ultrasound image P(i). If is not found, the process proceeds to step 12. The case where the high correlation portion 55 can be found in the ultrasound image P(i) corresponds to the case where the amount of movement of the body of the patient 34 is small and the target irradiation position T can be tracked. On the other hand, the case where the high correlation portion 55 cannot be found in the ultrasound image P(i) corresponds to the case where the amount of movement of the body of the patient 34 is large and the tracking of the target irradiation position T is impossible.

In step 6, the movement amount and movement direction from the position of the template 47 in the ultrasound image P(0) to the position of the high correlation portion 55 in the ultrasound image P(i) (hereinafter, the movement amount and the movement direction of the high correlation portion 55) are calculated by the misalignment detection unit 21. FIG. 7 shows an example of the movement amount and the movement direction of the high correlation portion 55.

The high correlation portion 55 is a portion of the body of the patient 34 that is likely to be the same as the portion represented by the template 47. The movement amount and the movement direction of the high correlation portion 55 are thus the movement amount and the movement direction of the body of the patient 34 from the time when the ultrasound image P(0) is acquired to the time when the ultrasound image P(i) is acquired. Therefore, the misalignment detection unit 21 detects the movement amount and the movement direction of the body of the patient 34 based on the movement amount and the movement direction of the high correlation portion 55.

In Step 7, the misalignment detection unit 21 estimates the target irradiation position T in the ultrasound image P(i). Both (i) the target irradiation position T and (ii) the template 47 or the high correlation portion 55 are located at a certain position with respect to the patient 34. Therefore, the positional relationship between (i) the target irradiation position T and (ii) the template 47 or the high correlation portion 55 is always constant. As a result, the movement amount and the movement direction from the target irradiation position T in the ultrasound image P(0) to the target irradiation position T in the ultrasound image P(i) are equal to the movement amount and the movement direction of the high correlation portion 55. The target irradiation position T in the ultrasound image P(0) is equal to the irradiation position F as described above. The target irradiation position T in the ultrasound image P(i) is a position moved from the irradiation position F by the movement amount of the high correlation portion 55 in the movement direction of the high correlation portion 55.

The misalignment detection unit 21 estimated the target irradiation position T in the ultrasound image P(i) to be located in a position which is moved from the irradiation position F in the movement direction of the high correlation portion 55 calculated in step 6 by the movement amount of the high correlation portion 55 calculated in step 6. FIG. 7 shows an example of the target irradiation position T in the ultrasound image P(i).

In step 8, the misalignment detecting unit 21 calculates the amount of misalignment between the target irradiation position T estimated in step 7 and the irradiation position F. Then, the misalignment detecting unit 21 determines whether the amount of the misalignment is smaller than a preset threshold. If the misalignment amount is smaller than the threshold value, the process proceeds to step 10. If the misalignment amount is equal to or greater than the threshold value, the process proceeds to step 9.

In step 9, the control unit 23 moves the position of the HIFU irradiation unit 33 using the robot control unit 9 and the robot arm 11 so that the irradiation position F and the target irradiation position T match.

In step 10, the control unit 23 determines whether a preset time has elapsed since the start of the irradiation of the focused ultrasound. If the preset time has elapsed, the process proceeds to step 12. If the preset time has not yet elapsed, the process proceeds to step 11.

In step 11, the control unit 23 increments the value of i by one. Thereafter, the process proceeds to step 4.

In Step 12, the control unit 23 stops the irradiation of the focused ultrasound by using the HIFU control unit 5.

The HIFU control unit 5 irradiates the focused ultrasound with a first output, and then irradiates the focused ultrasound with a second output smaller than the first output.

3. Effects of Control Apparatus 3

(1A) The control apparatus 3 detects a misalignment between the irradiation position F and the target irradiation position T. When detecting the misalignment, the control apparatus 3 brings the irradiation position F closer to the target irradiation position T. Thus, even if the body of the patient 34 moves during the treatment, it is possible to suppress irradiation of a position other than the target irradiation position T with the focused ultrasound. Further, even if the body of the patient 34 moves during the treatment, the target irradiation position T can be irradiated with the focused ultrasound.

(1b) When the movement amount of the patient 34 is large and the target irradiation position T cannot be tracked, the control apparatus 3 stops the irradiation of the focused ultrasound. Thereby, it is possible to suppress irradiation of a position other than the target irradiation position T with the focused ultrasound.

(1C) The control apparatus 3 acquires the ultrasound image P(0). In the ultrasound image P(0), the irradiation position F has a fixed positional relationship with the visual field 45. The control apparatus 3 extracts the template 47 from the ultrasound image P(0). The control apparatus 3 searches for the high correlation portion 55 in the ultrasound image P(i). The high correlation portion 55 is a portion corresponding to the template 47 in the body of the patient 34. The control apparatus 3 detects a movement amount and a movement direction of the high correlation portion 55. The control apparatus 3 detects a misalignment between the irradiation position F and the target irradiation position T based on the movement amount and the movement direction of the high correlation portion 55. Therefore, the control apparatus 3 can easily and accurately detect a misalignment between the irradiation position F and the target irradiation position T.

(1D) In the ultrasound images P(0) and P(n), a cavitation occurs near the irradiation position F, and the images change. The control apparatus 3 extracts the template 47 from the portion excluding the irradiation position F in the ultrasound image P(0). Therefore, the template 47 and the high correlation portion 55 hardly include such a cavitation. As a result, the high correlation portion 55 can be accurately searched.

(1E) The control apparatus 3 uses the HIFU control unit 5 to radiate focused ultrasound with a first output, and then radiate focused ultrasound with a second output smaller than the first output. Therefore, the cells in the affected area can be safely destroyed.

Second Embodiment

1. Differences from First Embodiment

Since the basic configuration of a second embodiment is the same as that of the first embodiment, differences will be described below. Note that the same reference signs as those in the first embodiment indicate the same configuration, and refer to the preceding descriptions.

In the first embodiment described above, the control apparatus 3 executes the processing shown in FIG. 4. The second embodiment is different from the first embodiment in that the control apparatus 3 executes the processing shown in FIG. 8.

2. Processing Executed by Control Apparatus 3

The processing executed by the control apparatus 3 will be described with reference to FIG. 8. This processing is executed after the operator 43 determines the target irradiation position T and starts irradiation of the focused ultrasound toward the target irradiation position T.

Figure 8:
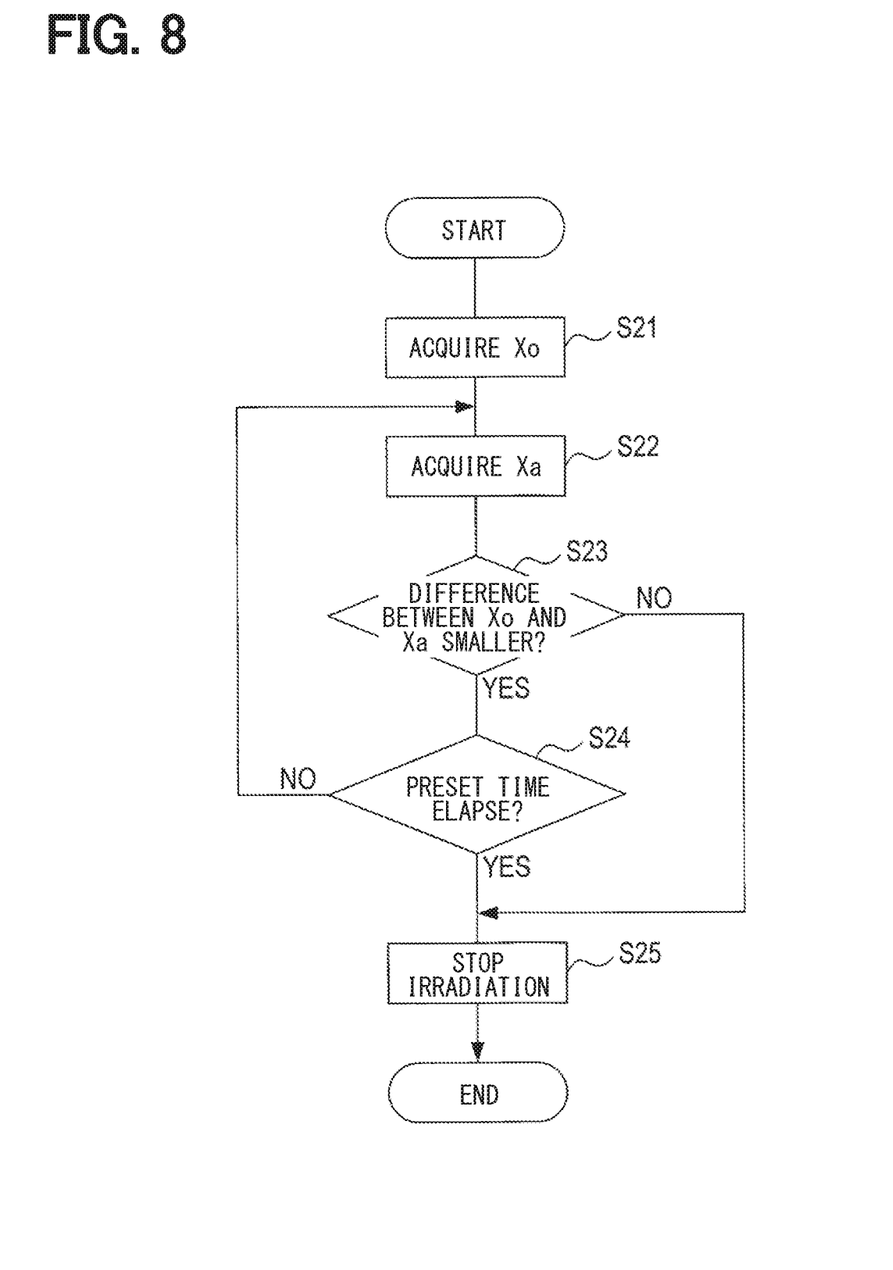
FIG. 8 is a flowchart illustrating a process executed by a control apparatus.

In step 21 in FIG. 8, the misalignment detection unit 21 uses the monitoring sense of force sensor 15 to detect the magnitude of the force applied by the body of the patient 34 to the tip unit 13. The magnitude of the force detected in step 21 is defined as Xo.

In step 22, the misalignment detection unit 21 uses the monitoring sense of force sensor 15 to detect the magnitude of the force applied by the body of the patient 34 to the tip unit 13. The magnitude of the force detected in step 22 is defined as Xa.

In step 23, the misalignment detection unit 21 determines whether the difference (hereinafter referred to as a force difference $\Delta X$) between the force magnitude Xa obtained in the previous step 22 and the force magnitude Xo is smaller than a preset threshold value. If the force difference $\Delta X$ is smaller than a threshold, the process proceeds to step 24. If the force difference $\Delta X$ is equal to or larger than the threshold, the process proceeds to step 25.

When the body of the patient 34 moves, the force difference $\Delta X$ increases. Further, when the body of the patient 34 moves, the misalignment between the irradiation position F and the target irradiation position T increases. That is, as the difference ΔX in force is larger, the misalignment between the irradiation position F and the target irradiation position T is larger.

In step 23, the difference ΔX in force corresponding to the misalignment between the irradiation position F and the target irradiation position T is detected, and it is determined whether the difference ΔX in force is smaller than a threshold value. This is equivalent to detecting a misalignment between the irradiation position F and the target irradiation position T and determining whether the amount of the misalignment is smaller than a threshold value.

In step 24, the control unit 23 determines whether a preset time has elapsed since the start of the irradiation of the focused ultrasound. If the preset time has elapsed, the process proceeds to step 25. If the preset time has not yet elapsed, the process proceeds to step 22.

In step 25, the control unit 23 stops the irradiation of the focused ultrasound by using the HIFU control unit 5.

3. Effects of Control Apparatus 3

According to the second embodiment described in detail above, the effect (1E) of the above-described first embodiment is obtained, and further, the following effects are obtained.

(2A) The control apparatus 3 detects a misalignment between the irradiation position F and the target irradiation position T. When the amount of misalignment is large, the control apparatus 3 stops the irradiation of the focused ultrasound. Thereby, it is possible to suppress irradiation of a position other than the target irradiation position T with the focused ultrasound.

(2B) The control apparatus 3 detects the magnitudes Xo and Xa of the force applied by the body of the patient 34 to the tip unit 13. The control apparatus 3 detects a misalignment between the irradiation position F and the target irradiation position T based on the fluctuation of the detected magnitudes Xo and Xa. Therefore, the control apparatus 3 can easily and accurately detect a misalignment between the irradiation position F and the target irradiation position T.

OTHER EMBODIMENTS

Although the embodiments of the present disclosure have been described above, the present disclosure is not limited to the embodiments described above, and various modifications can be made to implement the present disclosure.

Figure 9:
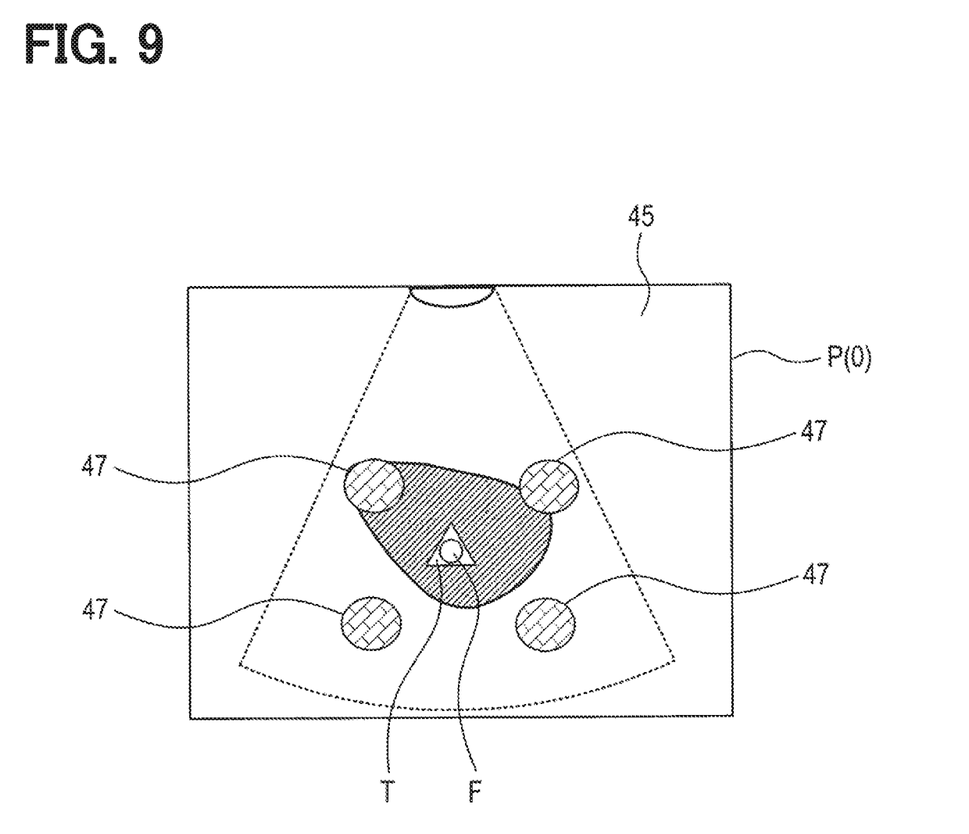
FIG. 9 is an explanatory diagram illustrating an ultrasound image and a plurality of templates.

(1) In the first embodiment, the misalignment detection unit 21 may extract a plurality of templates 47 from the ultrasound image P(0) as shown in FIG. 9. Each of the plurality of templates 47 is extracted from a portion excluding the irradiation position F.

As described in the above, in step 5, the misalignment detection unit 21 can search for the high correlation portion 55 for each of the plurality of templates 47. Suppose a case where the high correlation portion 55 cannot be found for some of the templates 47. In such a case, if the high correlation portion 55 is found for a certain number or more of the templates 47, the misalignment detection unit 21 performs an affirmative determination in step 5.

In step 6, the movement amount and movement direction of the high correlation portion 55 can be calculated for each of the plurality of high correlation portions 55. In step 7, the target irradiation position T in the ultrasound image P(i) can be estimated using, for example, the movement amounts and movement directions of the plurality of high correlation portions 55.

Figure 10:
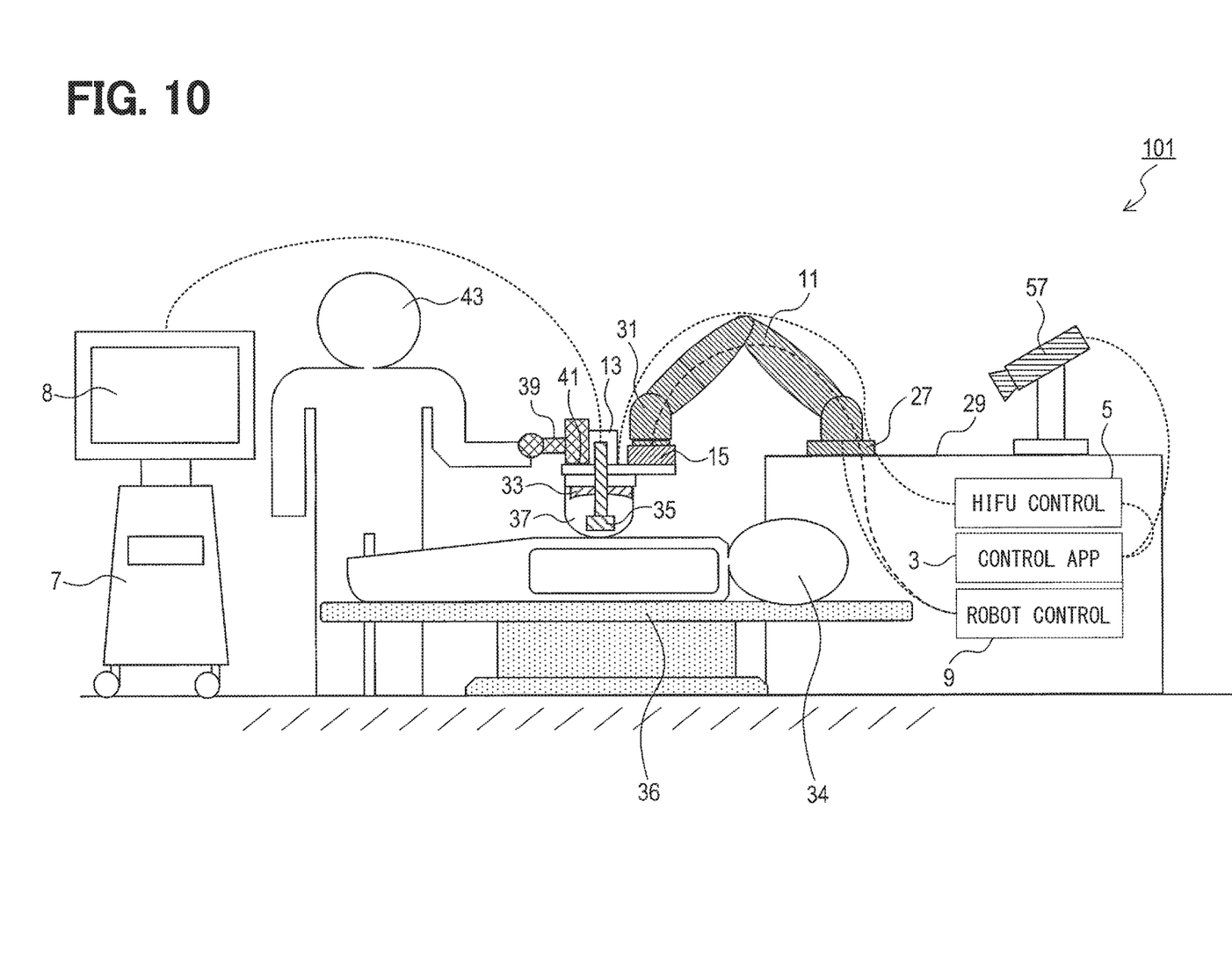
FIG. 10 is an explanatory diagram illustrating a configuration of a treatment system.

(2) The method by which the misalignment detection unit 21 detects the misalignment between the irradiation position F and the target irradiation position T may be another method. For example, as shown in FIG. 10, a treatment system 101 further includes a camera 57 in addition to the configuration of the treatment system 1. The camera 57 repeatedly shoots a range including the patient 34 at predetermined time intervals to create a plurality of images. The camera 57 outputs the plurality of created images to the control apparatus 3. The control apparatus 3 recognizes the body of the patient 34 in each of the plurality of images. The control apparatus 3 detects the movement of the patient 34 based on the change in the position of the patient 34 in the plurality of images.

When the body of the patient 34 moves, the irradiation position F and the target irradiation position T are misaligned. Therefore, the control apparatus 3 detecting the movement of the body of the patient 34 based on the change in the position of the body of the patient 34 in the plurality of images corresponds to the control apparatus 3 detecting a misalignment between the irradiation position F and the target irradiation position T.

Figure 11:
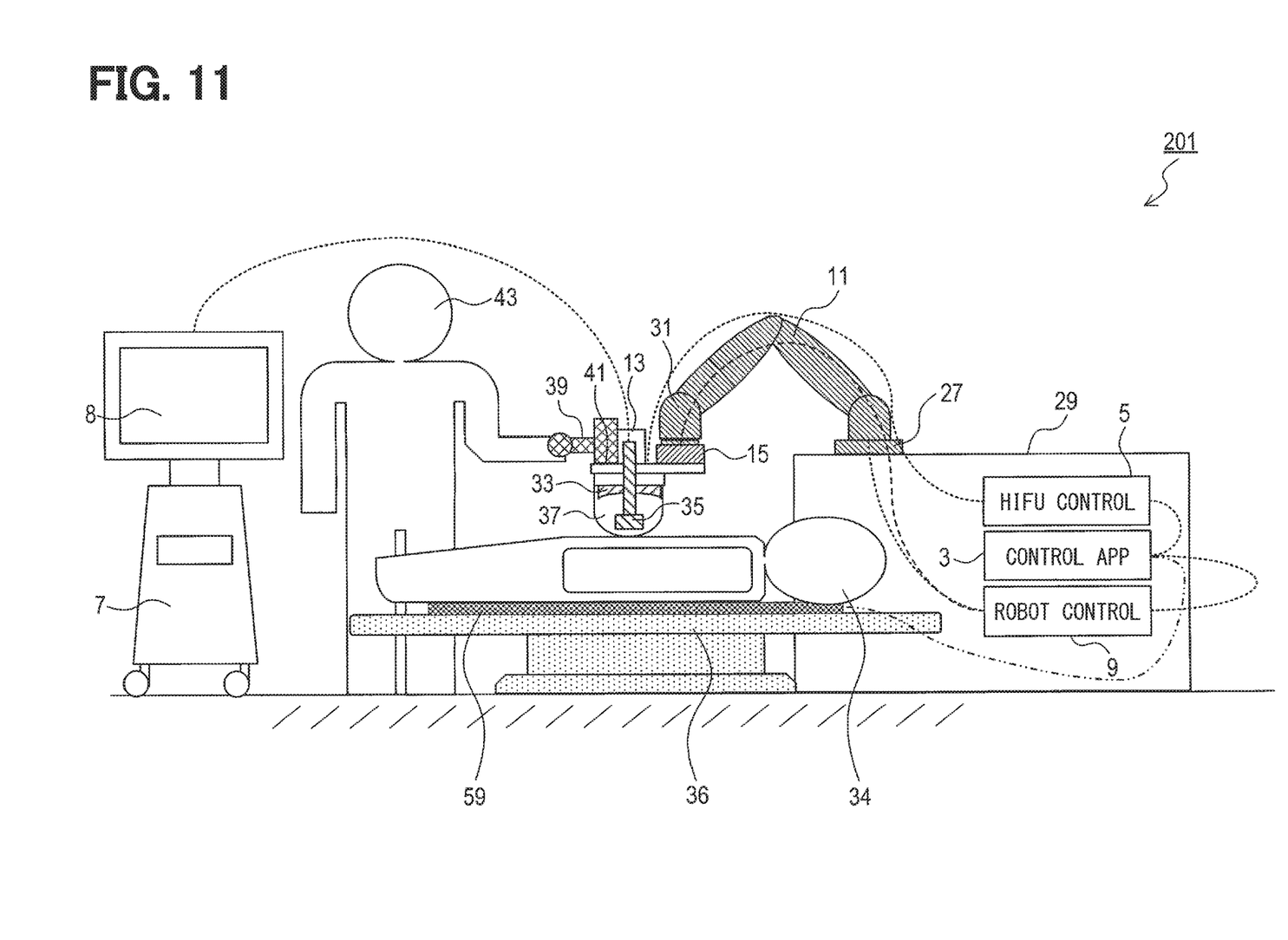
FIG. 11 is an explanatory diagram illustrating a configuration of a treatment system.

(3) The method by which the misalignment detection unit 21 detects the misalignment between the irradiation position F and the target irradiation position T may be another method. For example, as shown in FIG. 11, a treatment system 201 further includes a sheet-shaped pressure sensor 59 in addition to the configuration of the treatment system 1. The sheet-shaped pressure sensor 59 has a sheet-shaped form. The sheet-shaped pressure sensor 59 includes a plurality of pressure sensors. The plurality of pressure sensors are dispersedly arranged on the surface of the sheet-shaped pressure sensor 59. The patient 34 lies on the sheet-shaped pressure sensor 59. The sheet-shaped pressure sensor 59 outputs the detection results of the plurality of pressure sensors to the control apparatus 3. The control apparatus 3 detects the movement of the body of the patient 34 based on the change over time of the detection results of the plurality of pressure sensors.

When the body of the patient 34 moves, the irradiation position F and the target irradiation position T are misaligned. Therefore, the control apparatus 3 detecting the movement of the patient 34 based on the change over time of the detection results of the plurality of pressure sensors with the control apparatus 3 corresponds to the control apparatus 3 detecting the misalignment between the irradiation position F and the target irradiation position T.

(4) Instead of the HIFU irradiation unit 33, another transdermal treatment device may be used. Other transdermal treatment devices include, for example, a radiant ray irradiation device.

(5) In the first embodiment, the target irradiation position T may be estimated by a method of an optical flow.

(6) A plurality of functions of one element in the above embodiment may be implemented by a plurality of elements, or one function of one element may be implemented by a plurality of elements. Further, a plurality of functions of a plurality of elements may be implemented by one element, or one function implemented by a plurality of elements may be implemented by one element. A part of the configuration of the above embodiments may be omitted. At least a part of the configuration of the above embodiments may be added to or replaced with another configuration of the above embodiments. All examples included in the technical idea identified by the wording described in the claims correspond to embodiments of the present disclosure.

(7) The present disclosure can be realized in various forms, in addition to the control apparatus described above, such as a treatment system including the control apparatus as a component, a program for causing a computer to function as the control apparatus, a non-transitory tangible storage medium such as a semiconductor memory storing the program, or a control method of a treatment system.

For reference to further explain features of the present disclosure, the description is added as follows.

The HIFU treatment system includes an irradiation unit that irradiates the ultrasound. The ultrasound emitted from the irradiation unit focus on a focal point. Before irradiating the ultrasound, the operator moves the irradiation unit such that the irradiation position of the ultrasound coincides with a target irradiation position. The target irradiation position is an affected portion to be treated. Methods of confirming the irradiation position include a method using an ultrasound diagnostic probe, a method using MRI, and the like.

Detailed studies by the inventors have found the following issues. After starting radiating ultrasound, the patient's body may move. When the patient's body moves, the irradiation position is misaligned from the target irradiation position. In this case, the ultrasound is irradiated to a portion other than the target irradiation position.

It is thus desired to provide a control apparatus capable of suppressing irradiation to a portion other than a target irradiation position with a transdermal treatment device even when the patient's body moves during treatment.

An aspect of the present disclosure described herein is set forth in the following clauses.

According to an aspect of the present disclosure, a control apparatus is provided as including a misalignment detection unit and a control unit. The misalignment detection unit is configured to detect a misalignment between an irradiation position of a transdermal treatment device and a target irradiation position. In response to that the misalignment detection unit detects a misalignment, the control unit is configured to stop the irradiation of the transdermal treatment device or to bring the irradiation position closer to the target irradiation position.

Furthermore, the control apparatus may include one or more computers, which may include one or more processors; the one or more computers may serve as the misalignment detection unit and the control unit.

According to the control apparatus of the aspect of the present disclosure, even if a patient's body moves during treatment, a portion other than the target irradiation position may be suppressed from being irradiated with the transdermal treatment device.

What is claimed is:

1. A control apparatus for controlling an ultrasound control unit and a robotic arm control unit of a transdermal treatment device, the transdermal treatment device having;
the ultrasound control unit configured to control an output of high intensity focused ultrasound from a high intensity focused ultrasound irradiator;
a robotic arm having a force sensor and a tip unit disposed at one end thereof;
the robotic arm control unit configured to control a movement of the robotic arm, the force sensor, and the tip unit;
the tip unit including the high intensity focused ultrasound irradiator, wherein the tip unit is in communication with the ultrasound control unit and configured to contact a body of a patient, and wherein the high intensity focused ultrasound irradiator is configured to output a high intensity focused ultrasound to the body of the patient; and
the force sensor configured to measure forces applied to the tip unit by the body of the patient and to output force measurements to the robotic arm control unit, wherein
the ultrasound control unit and the robotic arm control unit are in communication with the control apparatus, and the control apparatus comprising:
one or more computers configured to:
output a first control instruction to the ultrasound control unit to start outputting the high intensity focused ultrasound from the high intensity focused ultrasound irradiator;
acquire a magnitude of a first force applied to the tip unit from the robotic arm control unit;
acquire a magnitude of a second force applied to the tip unit from the robotic arm control unit, after acquiring the magnitude of the first force;
determine whether a first difference between the magnitude of the first force and the magnitude of the second force is less than a threshold value to detect a misalignment between an irradiation position of the tip unit of the transdermal treatment device and a target irradiation position on the body of the patient based on the first difference between the magnitude of the first force and the magnitude of the second force relative to the threshold value; and
output a second control instruction to the ultrasound control unit to stop outputting the high intensity focused ultrasound from the high intensity focused ultrasound irradiator, in response to detecting the misalignment between the irradiation position of the tip unit of the transdermal treatment device and the target irradiation position on the body of the patient by determining that the first difference between the magnitude of the first force and the magnitude of the second force is equal to or greater than the threshold value;
determine whether a preset amount of time has elapsed after outputting the first control instruction to the ultrasound control unit, in response to determining the first difference between the magnitude of the first force and the magnitude of the second force is less than the threshold value;
output the second control instruction to the ultrasound control unit, in response to determining that the preset amount of time has elapsed;
acquire a magnitude of a third force applied to the tip unit from the robotic arm control unit after acquiring the magnitude of the first force and the magnitude of the second force, in response to determining that the preset amount of time has not elapsed;
determine whether a second difference between the magnitude of the first force and the magnitude of the third force is less than the threshold value based on the second difference between the magnitude of the first force and the magnitude of the third force relative to the threshold value; and
output the second control instruction to the ultrasound control unit to stop outputting the high intensity focused ultrasound from the high intensity focused ultrasound irradiator, in response to detecting the misalignment between the irradiation position of the tip unit of the transdermal treatment device and the target irradiation position on the body of the patient by determining that the second difference between the magnitude of the first force and the magnitude of the third force is equal to or greater than the threshold value.

2. A control apparatus for controlling an ultrasound control unit and a robotic arm control unit of a transdermal treatment device, the transdermal treatment device having:
   the ultrasound control unit, which is configured to control an output of high intensity focused ultrasound from a high intensity focused ultrasound irradiator;
   a robotic arm having a force sensor and a tip unit disposed at one end thereof; and
   the robotic arm control unit, which is configured to control movement of the robotic arm, the force sensor, and the tip unit;
   wherein:
   the tip unit includes the high intensity focused ultrasound irradiator, is in communication with the ultrasound control unit, and is configured to contact a body of a patient;
   the high intensity focused ultrasound irradiator is configured to output a high intensity focused ultrasound to the body of the patient;
   the force sensor is configured to measure forces applied to the tip unit by the body of the patient and to output force measurements to the robotic arm control unit;
   the ultrasound control unit and the robotic arm control unit are in communication with the control apparatus;
   the control apparatus includes:
      a misalignment detection unit configured to detect a misalignment between an irradiation position of the transdermal treatment device and a target irradiation position, after the transdermal treatment device starts an irradiation; and
      a control unit configured to start the irradiation by the transdermal treatment device and stop the irradiation by the transdermal treatment device in response to the misalignment detection unit detecting that the misalignment is equal to or greater than a threshold value;
   the misalignment detection unit is further configured to:
      acquire a magnitude of a first force applied to the tip unit from the robotic arm control unit at a first time after the irradiation by the transdermal treatment device is started;
      acquire repeatedly a magnitude of a present force applied to the tip unit from the robotic arm control unit at a present time, from when the magnitude of the first force is acquired to when a preset amount of time has elapsed; and
      detect that the misalignment is equal to or greater than the threshold value based on a variation from the magnitude of the first force to the magnitude of the present force.

* * * * *